United States Patent [19]
Büchi et al.

[11] 4,124,642
[45] Nov. 7, 1978

[54] 6,6,7-TRIMETHYL-TRICYCLO[5.2.2.0$^{1,5}$]UNDEC-8-EN-2-ONE

[75] Inventors: George H. Büchi, Cambridge, Mass.; Arnold Hauser, Petit-Lancy, Switzerland

[73] Assignee: Firmenich, S.A., Geneva, Switzerland

[21] Appl. No.: 834,777

[22] Filed: Sep. 19, 1977

[51] Int. Cl.$^2$ ............................................. C07C 49/54
[52] U.S. Cl. .............................. 260/586 G; 252/522; 260/586 C; 260/586 P
[58] Field of Search .................................... 260/586 G

[56] References Cited

U.S. PATENT DOCUMENTS

| | | |
|---|---|---|
| 3,836,584 | 9/1974 | Frater et al. ...................... 260/586 G |
| 3,925,479 | 12/1975 | Frater et al. ...................... 260/586 G |

*Primary Examiner*—Norman Morgenstern
*Attorney, Agent, or Firm*—Scully, Scott, Murphy & Presser

[57] ABSTRACT

Novel tricyclo-ketone derivatives useful as perfume ingredients and as intermediates for the preparation of (±) khusimone.

3 Claims, No Drawings

6,6,7-TRIMETHYL-TRICYCLO[5.2.2.0$^{1,5}$]UNDEC-8-EN-2-ONE

THE INVENTION

The present invention provides a novel tricycloketone of formula

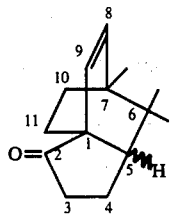

also defined as 6,6,7-trimethyl-tricyclo[5.2.2.0$^{1,5}$]undec-8-en-2-one.

Formula (I) defines the following epimers:

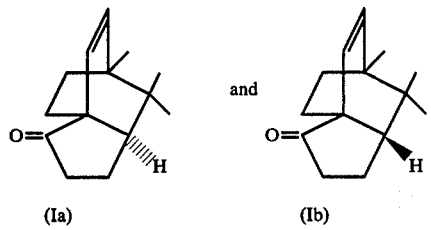

The invention relates also to a method for modifying the odoriferous properties of perfume compositions, perfume bases and perfumed articles, which method comprises the step of adding thereto an effective amount of 6,6,7-trimethyl-tricyclo[5.2.2.0$^{1,5}$]undec-8-en-2-one.

A further object of the present invention is to provide a process for the preparation of said 6,6,7-trimethyl-tricyclo[5.2.2.0$^{1,5}$]undec-8-en-2-one, which process comprises promoting an internal Diels-Alder reaction on a ketal of formula

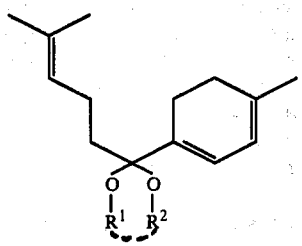

wherein R$^1$ and R$^2$, when taken separately, each represents a lower alkyl radical or, when taken together, a lower alkylene radical, by subjecting it to a thermal treatment and subsequently hydrolyzing the obtained reaction mixture.

Finally the invention relates to a process for the preparation of 7,7-dimethyl-6-methylene-tricyclo[6.2.1.0$^{1,5}$]undecan-2-one (hereinafter called "khusimone"), which comprises (a) isomerizing 6,6,7-trimethyl-tricyclo[5.2.2.0$^{1,5}$]undec-8-en-2-one by means of an acidic agent to give 6,7,7-trimethyl-tricyclo[6.2.1.0$^{1,5}$]undec-5-en-2-one (hereinafter called "isokhusimone");

(b) reacting the compound thus obtained with singlet oxygen followed by workup with a reducing agent to yield a tricyclo carbinol of formula

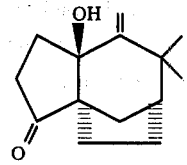

and (c) reducing said tricyclo carbinol by means of a metal in an acidic aqueous medium.

BACKGROUND OF THE INVENTION

Khusimone has been recognized as being mainly responsible for the characteristic scent of vetiver oil [Vetiveria zizanioides (L.) Nash], an important natural raw material currently used for compounding fine fragrance compositions [see e.g. Swiss Pat. No. 576,238, wherein its preparation, starting from natural occuring zizanoic acid, has been described]. Two total syntheses of starting zizanoic acid have been published in the scientific literature [see: Tetrahedron 27, 1481 (1971); Chem. Comm., 1335 (1969) and J. Chem. Soc. Perkin I, 1775 (1972)], however their interest is exclusively academic as they can not be industrially practicable.

By the process of the invention it is possible to prepare racemic khusimone starting from 6,6,7-trimethyl-tricyclo[5.2.2.0$^{1,5}$]undec-8-en-2-one, which compound can be obtained from easily available synthetic starting materials.

PREFERRED EMBODIMENTS OF THE INVENTION

According to an object of the present invention 6,6,7-trimethyl-tricyclo[5.2.2.0$^{1,5}$]undec-8-en-2-one is prepared by a process which consists in promoting an internal Diels-Alder reaction on ketal (II) by subjecting it to a thermal treatment followed by a hydrolysis of the obtained reaction mixture. The temperature necessary for effecting the said reaction can vary from about 200° to 250° C, preferably it is of about 220°-230° C. The reaction time can also vary within a wide range. It has been observed that when a temperature of 250° C is applied, 24 hours are sufficient to promote a satisfactory conversion of the starting undecenone. The Diels-Alder reaction can be effected at atmospheric pressure or at a higher pressure. Usually, it is convenient to operate in a sealed tube by heating the starting material in an inert organic solvent of high boiling point, such as substituted aromatic hydrocarbons, e.g. mesitylene. The subsequent hydrolysis of the obtained reaction mixture is carried out according to usual techniques, e.g. by treating said mixture in an acidic medium. Typically, perchloric acid in an aqueous ether, e.g. tetrahydrofuran, can be used to this end.

The desired 6,6,7-trimethyl-tricyclo[5.2.2.0$^{1,5}$]undec-8-en-2-one can be obtained in its pure form by subjecting the resulting hydrolyzed mixture to a column chromatography. A further chromatography separation on a silica gel column enabled to obtain the pure epimers of formula Ia and Ib. For practical and economic reasons this last step of separation is not required for most of the uses envisaged in the perfumery field, the two epimers having in fact analogous odoriferous properties.

6,6,7-Trimethyl-tricyclo[5.2.2.0$^{1,5}$]undec-8-en-2-one not only represents a valuable perfume ingredient in its own right but it is also a useful intermediate for the preparation of khusimone as defined by one of the processes of the invention, which process is better illustrated by the following reaction scheme:

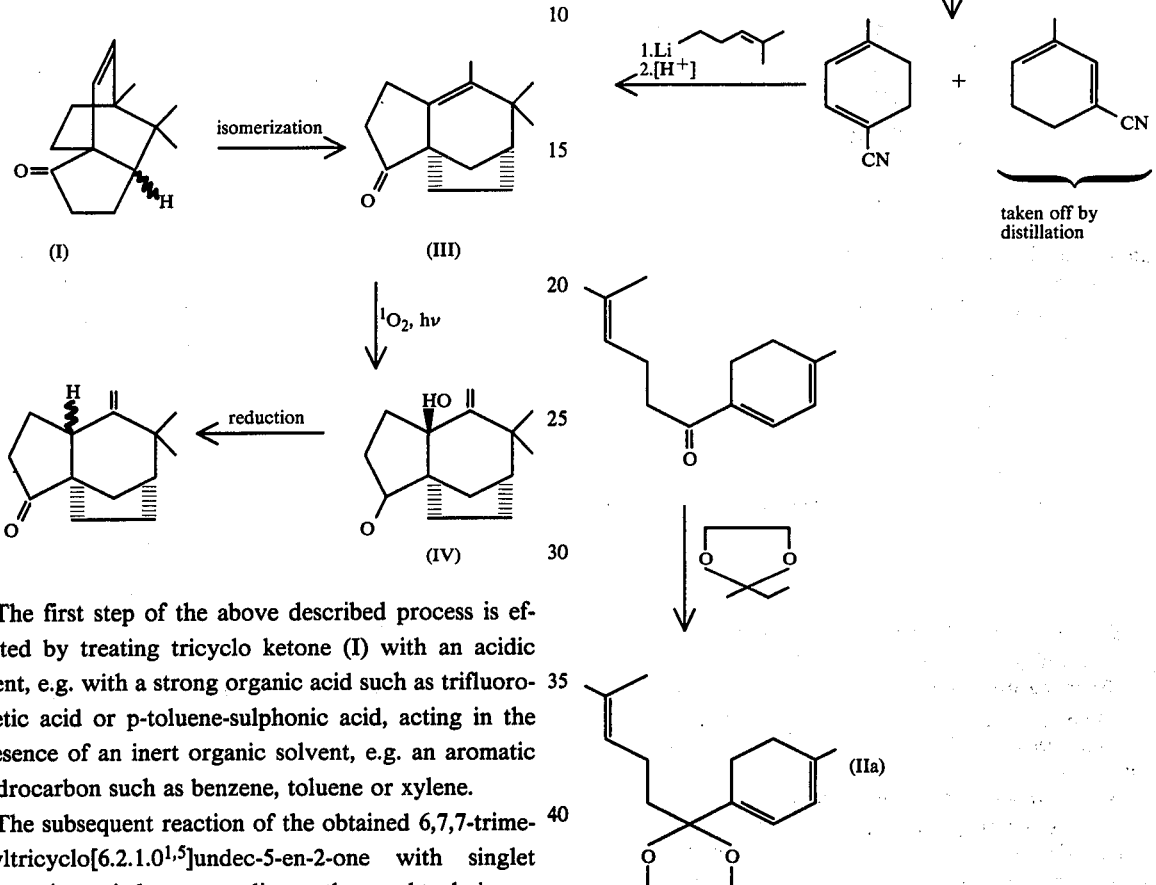

The first step of the above described process is effected by treating tricyclo ketone (I) with an acidic agent, e.g. with a strong organic acid such as trifluoroacetic acid or p-toluene-sulphonic acid, acting in the presence of an inert organic solvent, e.g. an aromatic hydrocarbon such as benzene, toluene or xylene.

The subsequent reaction of the obtained 6,7,7-trimethyltricyclo[6.2.1.0$^{1,5}$]undec-5-en-2-one with singlet oxygen is carried out according to the usual techniques, e.g. described in Accounts of Chem. Research 1, 104 (1968) [see also U.S. Pat. No. 3,723,271]. The subsequent reduction of the thus obtained reaction mixture by means of conventional reducing agents, such as triphenylphosphine, trimethyl or triethyl phosphite or sodium sulphite, gave unsaturated tricyclo carbinol (IV). -trimethyl-tricyclo[

This latter compound was further reduced by means of a metal in an acidic medium to yield the desired khusimone. The ketal of formula (II), the starting material for one of the processes of the invention, can be prepared according to the following synthetic method:

The above reaction pathway illustrates the preparation of the compound of formula (II) wherein R$^1$ and R$^2$, when taken together, represent an ethylene radical. It is obvious to those skilled in the art that an analogous method as that illustrated above can be followed also whenever R$^1$ and R$^2$ have different meaning within the definition given for formula (I).

6,6,7-Trimethyl-tricyclo[5.2.2.0$^{1,5}$]undec-8-en-2-one develops useful odoriferous properties, its fragrance character is typically woody and is reminiscent of the odour developed by oriental sandal-wood with certain nuances of vetiver oil. The obtained fragrance is very powerful and particularly suitable for the manufacture of perfumed articles destined to men-lines.

The proportions at which the cited compound can be used to promote the desired effects can vary within wide limits. Preferred concentrations range from about 2 to about 15% by weight based on the total weight of the composition to which the tricyclo ketone is added. It is however apparent to those skilled in the art that these limits are not absolute and values lower or higher than those cited may be used depending on the nature of the other perfume coingredients in a given composition or on the nature of the article it is desired to perfume. In the perfuming of toilet soaps, for instance, the preferred range can be as low as 0.5%.

The invention is better illustrated by but not limited to the following examples.

EXAMPLE 1

Melting points were determined in a Buchi apparatus and are uncorrected. Boiling points are uncorrected. Nuclear magnetic resonance (NMR) spectra were obtained using a Varian T-60. The chemical shift values are in parts per million downfield from internal teramethylsilane. Infrared spectra were recorded on a Perkin-Elmer 247. Mass spectra were determined with an Atlas $CH_4$, electron energy 70 eV; intensities of molecular ions ($M^+$) and fragment ions (highest peak of each group) are given as m/e in % of the most abundant peak (base peak = 100%). Gas chromatograms were run on a Perkin-Elmer 3920. The temperature are indicated in degrees centigrade.

6,6,7-trimethyl-tricyclo[5.2.2.0$^{1,5}$]undec-8-en-2-one

A solution of 1-[4-methyl-hexa-1,3-dien-1-yl]-5-methyl-hex-4-en-1-one ethylene ketal (449 mg, 1.8 mmol) in mesitylene (40 ml) was heated at 225° in a sealed tube for 4 days. The solvent was removed in vacuo and the mixture of ketals was hydrolyzed overnight at room temperature in tetrahydrofuran (10 ml), water (4 ml) and perchloric acid 70% (0.2 ml). Sodium bicarbonate (1 g) was added and the tetrahydrofuran was distilled off under reduced pressure. The residue was extracted with ether (3 × 25 ml) and the combined ether layers were washed (water, brine), dried ($Na_2SO_4$) and concentrated to afford 365 mg of a crude mixture of ketones which was chromatographed on silica gel using 98:2 hexane/ethyl acetate. The first fraction gave 173 mg (47%) of an aromatic ketone and the second, eluted with 95:5 hexane/ethyl acetate, afforded 147 mg (40%) of the desired tricyclo ketone as a mixture of two isomers. These were separated by a second chromatography on silica gel and crystallization of the two products from pentane gave the analytical samples. Isomer (Ia):mp 64°–65°;

IR($CHCl_3$): 1735 cm$^{-1}$;

NMR($CCl_4$): 6.04 (1H, d, J = 8 Hz), 5.78 (1H, d, J = 8 Hz), 1.2-2.7 (9H, m), 1.08 (1H, s), 1.04 (1H, s), 0.81 (3H, s) δ ppm;

MS : 204 ($M^+$, 100); m/e: 189 (65), 171 (3), 161 (23), 147 (10), 136 (61), 121 (88), 105 (18), 91 (29), 77 (23), 69 (13), 55 (10), 41 (25).

Isomer (Ib): mp 37.5°–38.5°;
IR($CHCl_3$): 1735 cm$^{-1}$;
NMR($CCl_4$): 6.28 (1H, d, J = 8 Hz), 5.85 (1H, d, J = 8 Hz), 1.2-2.6 (9H, m), 1.10 (3H, s), 0.94 (3H, s), 0.83 (3H, s) δ ppm;

MS: 204 ($M^+$, 100); m/e: 189 (59), 161 (23), 147 (10), 136 (58), 121 (79), 105 (18), 94 (31), 77 (34), 69 (13), 55 (11), 41 (28).

1-[4-methyl-hexa-1,3-dien-1-yl]-5-methyl-hex-4-en-1-one ethylene ketal, used as starting material in the hereinabove described process can be prepared as follows:

a. A mixture of 2-chloroacrylonitrile (17.5 g, 0.2 mol), isoprene (20.4 g, 0.3 mol) and 2,5-di-tert-butylhydroquinone (300 mg) were heated in a sealed tube at 100° for 15 hours. After removal of the excess isoprene the residue was distilled to yield 25.8 g (83%) of 4-methyl-and 3-methyl-hex-4(3)-enchloronitrile: bp 65°–70° C (0.5 mm). (According to the NMR the product contains about 30% of 3-methyl isomer) IR($CCl_4$): 3040, 2245, 1680 cm$^{-1}$;

NMR($CCl_4$): 5.49 (0.3 H, b), 5.27 (0.7 H, b), 2.70 (2 H, b), 2.29 (4H, s), 1.77 (3 H, d, J = 2 Hz);

MS: 155 ($M^+$, 24); m/e: 140 (< 1), 128 (< 1), 120 (15), 104 (19), 93 (23), 77 (12), 68 (100), 53 (13), 39 (17).

b. To a stirred solution of the obtained mixture of chloronitrile (108.5 g, 0.7 mol) in tetrahydrofuran (100 ml) was slowly added 1,5-diazabicyclo[3.4.0]non-5-ene (DBN) (89.3 g, 0.72 mol) in tetrahydrofuran (100 ml) at 0° – 5°. Stirring was continued at room temperature overnight and then water (100 ml) was added. The mixture was extracted twice with ether and the combined extracts were washed with 1 N $H_2SO_4$ (2 × 50 ml), water (3 × 50 ml) and brine (50 ml), dried ($Na_2SO_4$) and concentrated. Spinning band distillation of the residue gave 45.0 g (53%) of pure dienenitrile of formula

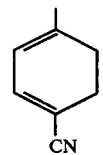

IR($CCl_4$): 3060, 2210, 1645, 1585, 830 cm$^{-1}$; UV max (95% EtOH) 295 nm (ε 9950);

NMR($CCl_4$): 6.50 (1H, d, J = 6 Hz), 5.73 (1H, m), 2.29 (4H, s), 1.87 (3H, d, J = 2 Hz) ε ppm MS: 119 ($M^+$, 57); m/e: 104 (100), 91 (33), 77 (30), 65 (6), 51 (9), 39 (15).

c. The obtained dienenitrile (23.8 g, 0.2 mol) in absolute ether (200 ml) was added dropwise at −78° to a stirred ethereal solution of 5-lithio-2-methyl-pent-2-ene, prepared at −10° from 5-bromo-2-methyl-pent-2-ene, as described in Bull. Soc. Chim. France 1072 (1960), (48.9 g, 0.3 mol) in abs. ether (300 ml) and lithium containing 1% sodium (8.4 g, 1.2 mol). The resulting dark red solution was stirred an additional 3/4 hour at −78° and then hydrolyzed with water (100 ml) and $NH_4Cl$ sat. (100 ml). The ketimine was separated from the neutral parts of the ether layer by extraction with 1 N HCl (1 × 100 ml. 3 × 50 ml). The combined extracts were stirred with ether (200 ml) at room temperature for 24 hours and then layers were separated. After this procedure has been repeated once, the ether layers, containing the ketone, were united, washed (water, $NaHCO_3$ sat. and brine), dried ($Na_2SO_4$), concentrated and distilled to give 31.8 g (78%) of the dieneketone of formula

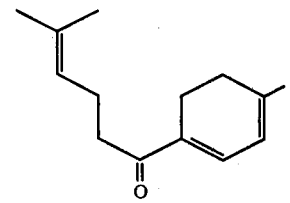

bp 94°–95° (0.02 Torr);

IR($CHCl_3$): 3050, 1660, 1585, 1170 cm$^{-1}$; UV max (95% EtOH) 315 nm (ε 11700);

NMR($CCl_4$): 6.71 (1H, d, J = 6 Hz), 5.74 (1H, d with fine splitting, J = 6 Hz), 5.02 (1H, t, J = 7 Hz), 2.0–2.8 (8H, m), 1.87 (3H, s), 1.65 (3H, s), 1.62 (3H, s) ε ppm;

MS: 204 (M+, 82); m/e: 189 (45), 175 (1), 161 (15), 147 (8), 136 (46), 121 (100), 105 (14), 91 (49), 77 (44), 69 (23), 55 (15), 41 (39).

d. A solution of dieneketone, obtained as described sub letter c. above, (408 mg, 2 mmol) and p-toluene sulfonic acid monohydrate (20 mg) in butanone ethyleneketal [see: J.Am.Chem.Soc., 76, 1359 (1954)] (5 ml) was heated in an oil bath (120°) and the liberated butanone, admixed with butanone ethyleneketal was distilled off during a period of 15 hours. About 2 ml of distillate was collected. The reaction mixture was diluted with hexane (50 ml), washed (NaHCO$_3$ sat., water and brine), dried (Na$_2$SO$_4$) and concentrated in vacuo. The resulting mixture of starting material and ketal was chromatographed on silica gel using 95:5 hexane/ethyl acetate. Bulb distillation 130° (0.1 Torr) gave 227 mg (80.3%) of desired dieneketal of formula

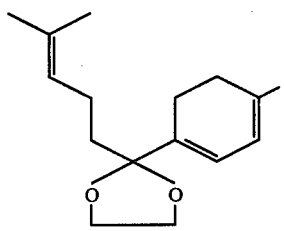

(Yield based on recovered starting material (175 mg).

IR(CHCl$_3$): 3050, 1610, 1040 cm$^{-1}$;

NMR(CCl$_4$): 5.86 (1H, d, J = 6 Hz), 5.59 (1H, d with fine splitting, J = 6 Hz), 5.05 (1H, t with fine splitting, J = 6 Hz), 3.80 (4H, s), 2.10 (4H, s), 1.80 (3H, d, J = 6 Hz), 1.69 (3H, s), 1.61 (3H, s), 1.6–2.5 (4H, m) ε ppm

EXAMPLE 2

Khusimone a. A solution of p-toluenesulfonic acid monohydrate (334 mg, 1.76 mmol) in benzene (4 ml) was refluxed (Dean-Stark separator) for ½ hour before 6,6,7-trimethyl-tricyclo [5.2.2.0$^{1,5}$]undec-8-en-2-one, (isomer (Ia), (90 mg, 0.44 mmol) in benzene (1 ml) was added at room temperature. Stirring was continued under reflux for 15 hours and thereafter the mixture was cooled and diluted with ether (10 ml) and poured into chilled, saturated NaHCO$_3$-solution. The ether layer was washed (water, brine), dried (Na$_2$SO$_4$) and concentrated. Bulb distillation at 120° (0.1 Torr) gave 76 mg (84.5%) of a mixture is isokhusimone (ca. 30%) and a ketone of formula

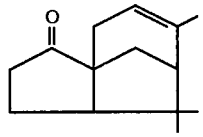

(ca. 70%) which was separated by preparative gas chromatography to give 13.5 mg (15%) of isokhusimone:
IR(CHCl$_3$): 1735 cm$^{-1}$;

NMR(CCl$_4$): 1.5–2.8 (11H, m), 1.50 (3H, s with fine splitting), 1.06 (6H, s) δ ppm;

MS: 204 (M+, 43); m/e: 189 (66), 161 (43), 148 (11), 133 (34), 119 (100), 105 (11), 91 (14), 77 (7), 69 (5), 55 (5), 41 (16).

The spectra are identical with (−)-isokhusimone, made by p-TsOH treatment of (−)-khusimone in benzene.

6,6,7-Trimethyl-tricyclo[5.2.2.0$^{1,5}$]undec-8-en-2-one, isomer (Ib), was treated the same way as described for isomer Ia above, but was only refluxed for 5 hours. Yield: 44% of pure isokhusimone purified by gas chromatography.

b. A solution of isokhusimone (130mg, 0.64 mmol) and Rose Bengal (10 mg in 1:1 MeOH/water) in ethanol (120 ml) was irradiated under a slow oxygen stream in a Pyrex tube with a Hanovia 200 W mercury medium pressure lamp for 1½ hours. During this time, the temperature was kept at ca. 25° with a waterbath. Then trimethyl phosphite (158 mg, 1.28 mmol) was added and the mixture was stirred overnight at room temperature and then concentrated in vacuo. The crude product was chromatographed on silica gel with 9:1 hexane/ethyl acetate to give 109 mg (77.4%) of carbinol(IV):

mp 107°–110° (from CCl$_4$);

IR(CHCl$_3$): 3630, 3450, 1740, 1640, 920 cm$^{-1}$;

NMR(CCl$_4$): 4.98 (1H, s), 4.92 (1H, s), 1.0–2.5 (12H, m, s at 1.80 exchanges with D$_2$O), 1.27 (3H, s), 1.10 (3H, s) δ ppm;

MS: 220 (M+, 100); m/e: 205 (41), 192 (28), 177 (54), 159 (54), 149 (36), 131 (28), 123 (99.5), 109 (32), 91 (37), 79 (25), 67 (32), 55 (38), 41 (53).

c. The carbinol obtained in accordance to letter b. above was reduced with amalgated zinc powder and ethereal HCl at −15°, in accordance with the method described in Tetrahedron Letters 725 (1972), to give a 75.2% yield of a mixture of (±)-khusimone (ca 70%) and (±)-epikhusimone (ca 30%) of formula

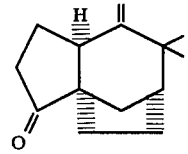

EXAMPLE 3

A perfume composition for men "eau-de-toilette" was prepared by admixing the following ingredients (parts by weight):

| Ingredient | Parts |
|---|---|
| Coumarin | 80 |
| Musk xylene | 70 |
| Synthetic bergamot | 100 |
| Lavandin oil | 150 |
| Linalyl acetate | 100 |
| Coriander | 30 |
| Benzyl acetate | 50 |
| Amyl salicylate | 50 |
| Canaga oil | 20 |
| Benzyl salicylate | 50 |
| Patchouli | 30 |
| Synthetic geranium | 100 |
| Clove oil | 20 |
| Benzoin resinoide | 50 |
| 6,6,7-Trimethyl-tricyclo[5 . 2 . 2 . 0$^{1,5}$] undec-8-en-2-one | 100 |
| | 1000 |

The addition of 6,6,7-trimethyl-tricyclo[5.2.2.0$^{1,5}$]undec-8-en-2-one to the composition brings about a character of originality and distinct elegance.

What I claim is:

1. 6,6,7-Trimethyl-tricyclo[5.2.2.0$^{1,5}$]undec-8-en-2-one.

2. The compound of claim 1 in its epimeric form of formula

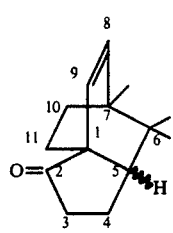
(Ia)
3. The compound of claim 1 in its epimeric form of formula
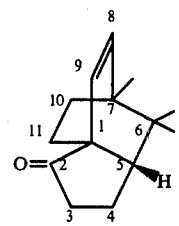
(Ib)
* * * * *

UNITED STATES PATENT AND TRADEMARK OFFICE
CERTIFICATE OF CORRECTION

PATENT NO. : 4,124,642
DATED : November 7, 1978
INVENTOR(S) : Büchi et al.

It is certified that error appears in the above-identified patent and that said Letters Patent are hereby corrected as shown below:

Col. 2, line 31, the word "pure" should be inserted before the word "racemic".

Col. 3, line 52, "-trimethyl-tricyclo[" should be deleted.

Col. 5, line 11, "terame-" should read as --tetrame---

Col. 6, line 31, "$\epsilon$" should read as --$\delta$--.

Col. 7, line 34, "$\epsilon$" should read as --$\delta$--.
Col. 6, line 68, "$\epsilon$" should read as --$\delta$--.

Signed and Sealed this

Twenty-seventh Day of March 1979

[SEAL]

Attest:

RUTH C. MASON
Attesting Officer

DONALD W. BANNER
Commissioner of Patents and Trademarks